United States Patent [19]
Sanberg et al.

[11] Patent Number: 5,830,460
[45] Date of Patent: Nov. 3, 1998

[54] SERTOLI CELLS AS TRANSPLANTATION FACILITATOR FOR CELL TRANSPLANTATION

[75] Inventors: Paul R. Sanberg, Spring Hill; Don F. Cameron; Cesario V. Borlongan, both of Lutz; Richard Heller, Brandon, all of Fla.

[73] Assignee: University of South Florida, Tampa, Fla.

[21] Appl. No.: 402,387

[22] Filed: Mar. 13, 1995

[51] Int. Cl.⁶ .................................................. C12N 5/00
[52] U.S. Cl. .......................... 424/93.7; 424/93.1; 424/559
[58] Field of Search .................................. 424/93.1, 93.7, 424/559

[56] References Cited

FOREIGN PATENT DOCUMENTS

WO9528167  10/1995  WIPO.

OTHER PUBLICATIONS

Berden et al., "Severe central nervous system toxicity associated with cyclosporine" *Lancet* 26:219–220 (1985).

Bjorklund and Stenevi, "Intracerebral neural grafting: a historical perspective" in Bjorklund, A. and U. Stenevi, eds. *Neural grafting in the mammalian CNS*, Amsterdam: Elsevier, 3–11 (1985).

Bjorklund, "Dopaminergic transplants in experimental Parkinsonism: cellular mechanisms of graft–induced functional recovery" Current Opinion in Neurobiology 2:683–689 (1992).

Borlongan et al., "Cyclosporine–A increases spontaneous and dopamine agonist–induced locomotor behavior in normal rats" *Cell Transplant.*, 4:65–73 (1995).

Cameron et al., "Successful islet/abdominal testis transplantation does not require Leydig cells" *Transplantation*, 50:649–653 (1990).

Cameron and Muffly, "Hormonal regulation of spermatid binding" *J. Cell Sci.*, 100:632–633 (1991).

de Groen et al., "Central nervous system toxicity after liver transplantation" *N. Engl. J. Med.*, 317(14):861–866 (1984).

Freeman et al., "The USF protocal for fetal nigral transplantation in Parkinson's disease" Amer. Soc. for Neural Transplantation 1:29, Abstract, No. 535.

Griswold, "Protein secretion by sertoli cells: general considerations" in Russell, L.D. and M.D. Griswold, eds. *The Sertoli Cell*, Cache River Press, Clearwater, FL, 195–200.

Isacson, et al., "Graft–induced behavioral recovery in an animal model of Huntington's disease" *Proc. Natl. Acad. Sci.*, 83:2728–2732 (1986).

Lindvall et al., "Transplantation in Parkinson's disease: two cases of adrenal medullary grafts to the putamen" *Ann. Neurol.*, 22:457–468 (1987).

Lindvall et al., "Grafts of fetal dopamine neurons survive and improve motor function in Parkinson's disease" *Science*, 247:574–577 (1990).

Pakzaban et al., "Increased proportion of Ache–rich zones and improved morphological integration in striatum of fetal grafts . . ." *Exp. Brain Res.*, 97:13–22 (1993).

Paxinos and Watson, "The rat brain in stereotaxic coordinates" Sydney, Academic Press (1984).

Sagen et al., "Transplants of immunologically isolated xenogeneic chromaffin cells provide a long–term source of pain–reducing . . ." *J. Neurosci.*, 13:2415–2423 (1993).

Sanberg et al., "Transplantation into the central nervous system" in *Cell Transplantation for Huntington's Disease*, R.G. Landes, Co., Boca Raton, FL, Chap. 4, pp. 19–21 (1994).

Selawry and Cameron, "Sertoli cell–enriched fraction in successful islet cell transplantation" *Cell Transplant.*, 2:123–129 (1993).

Wictorin et al., "Reformation of long axon pathways in adult rat CNS by human forebrain neuroblasts" *Nature*, 347:556–558 (1990).

Koutouzis et al. "Cell Transplantation for Central Nervous System Disorders" *Critical Reviews in Neurobiology*, 8(3):125–162 (1994).

Sigma Chemical Company Catalog (1992), pp. 1670–1673.
Bellgrau et al (1995) Nature 377:630–632.
DeCesaris et al (1992) EDS–Rivista Di Immunologia ed Immunofarmacologia 12(2):86.
Sanberg et al (1995) Soc. for Neurosci. Abstr. 21:317.

*Primary Examiner*—Lila Feisee
*Assistant Examiner*—Minh-Tam B. Davis
*Attorney, Agent, or Firm*—Kohn & Associates

[57] ABSTRACT

A method of producing a sustained localized brain immunosuppressive effect in localized tissues is achieved by transplanting Sertoli cells proximate to the brain tissue.

4 Claims, 3 Drawing Sheets

SERTOLI CELLS AS TRANSPLANTATION FACILITATOR FOR CELL TRANSPLANTATION

TECHNICAL FIELD

The present invention relates to neural pharmacology and specifically to methods of transplanting cells to create a localized immunosuppressive effect in tissue.

BACKGROUND OF THE INVENTION

The central nervous system (CNS) has poor regenerative capacity which is exemplified in a number of neurodegenerative disorders. An example of such a disorder is Parkinson's disease. The preferred pharmacotherapy for Parkinson's disease is L-dopa which does slow the progression of this disease in some humans. However, the neuropathological damage and the consequent behavioral deficits is not reversed by this treatment protocol.

Laboratory and clinical studies have shown the transplantation of cells into the CNS is a potentially significant alternative therapeutic modality for neurodegenerative disorders such as Parkinson's disease (Wictorin et al., 1990; Lindvall et al., 1990; Sanberg et al., 1994; Bjorlund and Stenevi, 1985; Freeman et al., 1994). In some cases, transplanted neural tissue can survive and form connections with the CNS of the recipient (i.e. the host). When successfully accepted by the host, the transplanted tissue (i.e. the graft) has been shown to ameliorate the behavioral deficits associated with the disorder (Wictorin et al., 1990). The obligatory step for the success of this kind of treatment is the prevention of graft rejection (i.e. graft acceptance).

Currently, fetal neural tissue is the primary graft source for neural transplantation (Lindvall et al., 1990; Bjorklund, 1992; Isacson et al., 1986; Sanberg et al., 1994). Other viable graft sources include adrenal chromaffin cells and various cell types that secrete nerve growth factors and trophic factors. The field of neural tissue transplantation as a productive treatment protocol for neurodegenerative disorders has received much attention resulting in its progression to clinical trials. Preliminary results and clinical observations are promising although the graft rejection phenomenon remains problematic.

Recently, studies have suggested that Sertoli cells, when simultaneously transplanted with pancreatic islet cell into the diabetic rat, act as an effective local immunosuppressant on the host tissue (Selawry and Cameron, 1993). As a result, the graft is not rejected and the islets remain viable allowing the transplanted β-cells to function normally and produce insulin for an indefinite period of time. As a result, the accepted graft overcomes the primary physiological dysfunction of hyperglycemia thereby alleviating the related complications of this endocrine disorder. This cell transplantation protocol is accomplished without prolonged systemic immunosuppression, otherwise necessary when islets are transplanted without Sertoli cells.

In general, systemic immunosuppression is necessary if successful transplantation is to be achieved in humans. Immunosuppression of the entire body (i.e. systemic) can result, eventually, in graft acceptance. It is acquired, however, by placing the individual at medical risk making the immunosuppressant therapy itself more of a liability than a benefit in some cases. For a lack of a better immunosuppressant treatment, systemic immunosuppressants, with Cyclosporine-A (CsA) as the treatment choice, have been used as adjunctive therapy in neural transplantation protocols (Sanberg et al., 1994; Freeman et al., 1994; Borlongan et al., 1995). Arguably, systemic CsA treatment may be contraproductive to successful graft acceptance in the CNS because of its systemic effect and because CsA itself has been shown to cause detrimental side effects and may, in fact, be cytotoxic to neural tissues (Berden et al., 1985; deGroen et al., 1984).

It would be desirable to enhance the productive cell transplantation techniques already utilized for neurodegenerative disorders, such as Parkinson's disease, in ways which would more effectively slow the neurodegenerative disease process, more actively promote the re-establishment of normal neural tissue physiology and better alleviate the functional disabilities associated with the neural tissue dysfunction. Likewise, it would be desirable to avoid systemic immunosuppression with the ability to immunosuppress locally (i.e. at the graft site) by an immunosuppressant which is biologically tolerated by the host. Sertoli cells may provide this desired option since it is clear from the diabetic studies, as summarized above, that co-transplantation with Sertoli cells will deliver local immunosuppression and promote, therefore, efficient graft acceptance and functional restoration of the tissue-related dysfunction.

SUMMARY OF THE INVENTION AND ADVANTAGES

In accordance with the present invention, there is provided a method of producing a sustained localized immunosuppressive effect in tissue by transplanting Sertoli cells proximate to the tissue.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
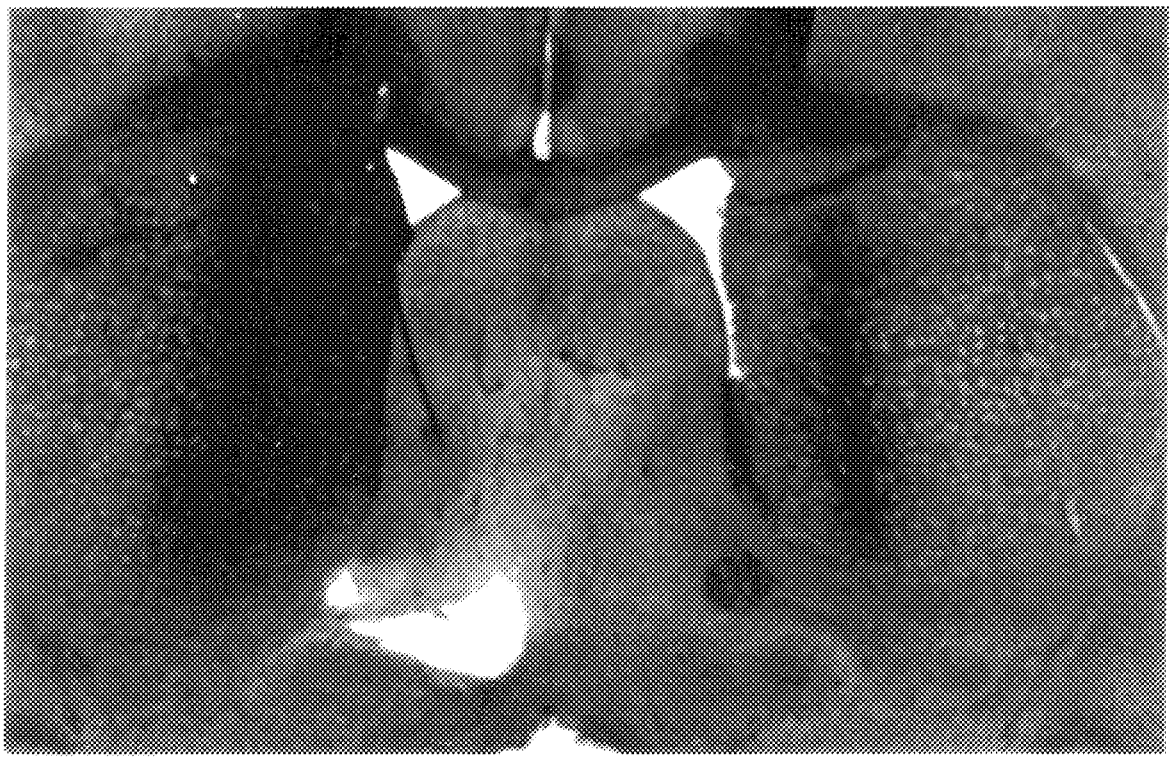
FIGS. 1a–b shows photomicrographs of two representative brain sections wherein the sections were stained with Lectin, the left side of each brain corresponds to the chromaffin cells transplanted side while the right side of each brain corresponds to the chromaffin cells with Sertoli cells transplanted side

The present invention provides a method of producing a sustained localized immunosuppressive effect in tissue. This is achieved by the general step of transplanting Sertoli cells proximate to the tissue.

By sustained localized immunosuppressive effect, it meant that the transplanted Sertoli cells will suppress the immunological response ordinarily mounted by the host tissue to the intrusion of foreign entities such as transplanted cells and that the immunosuppression will occur at the graft site (local) rather than by generalized immunosuppression of the entire body (systemic) which occurs with the ordinary methods of immunosuppression by agents such as CsA.

In a preferred embodiment, the transplanted cells (which are intended to replace the dysfunctional cells or in some way alleviate neural tissue dysfunction) can avoid being rejected and thereby effectively survive and form functional cell-to-cell connections with the host tissue. This then will promote re-establishment of normal neural tissue function and thereby ameliorate the behavioral deficits associated with the neurodegenerative disorder being treated. However, the method of the present invention can also be utilized with transplantable cells other than neural tissue/cells such as endocrine cells, muscle cells, and other cells by utilizing similar techniques as those described for neural cells. That is, Sertoli cells are used to facilitate transplant survival and transplant function of the cells being transplanted.

With local immunosuppression by a Sertoli cell-derived immunosuppressant agent (which is now partially characterized), there would be no successful antibody or cellular immunological attack waged against the transplanted cells, including the Sertoli cells themselves. Additionally, since the immunosuppression is local and by a biologically tolerable agent, the side effects associated with both systemic immunosuppression and cytotoxicity of agents such as CsA would be avoided. Hence, the method of Sertoli cell transplantation provides a significant improvement over the use of systemic immunosuppression with CsA as the necessary adjunctive therapy to neural transplantation.

The source of Sertoli cells is by primary cell isolation from the mammalian testis. The protocol for harvesting the cells is well-defined (Cameron and Muffly, 1991; Griswold, 1992) and considered a routine methodology. In most of the published reports of Sertoli cell co-transplantation, cells are derived from the rat (Selawry and Cameron, 1993).

Specifically, the Sertoli cells are co-transplanted with the selected neural tissue into the CNS by intracranial infusion (Sanberg et al., 1995).

By proximate to the tissue, it is meant that the Sertoli cells are placed in general proximity to the selected tissue such as the neural tissue. Generally, this means that the Sertoli cells can be infused or transplanted into any mammal so as to become located in proximity to the selected tissue. For example, the location can be any site where tissue is innervated such as the CNS, PNS, fluids such as cerebral spinal fluid and blood, blood vessels, endothelial tissue, muscle tissues, end organs, etc. The proximity of the Sertoli cells to the neural tissue is only limited by the specific neural cells and function sought to be restored in a given transplantation.

The source of neural cells for transplantation depends on the neurological disorder being treated. For example, Parkinson's disease is treated with ventral mesencephalic tissue (Lindvall et al., 1990) or chromaffin cells (Lindvall et al., 1987), Huntington's disease is treated with striatal lateral eminence cells (Isacson et al., 1986) and neurological pain is treated with adrenal chromaffin cells (Sagen et al., 1993). Other tissue types experimentally transplanted into specific animal models of human neurodegenerative disorders are summarized elsewhere (Dunnett and Bjorklund, 1994) and provide detailed descriptions of cell isolation and transplantation methods.

The following examples demonstrate the methods of use of the present invention as well as efficacy for producing a sustained localized immunosuppressive effect.

Materials and Methods

Sprague-Dawley male rats, six weeks old, which were obtained from Harlan Sprague-Dawley, Inc. (Indianapolis, Ind.), were used. The animals were housed in individual Plexiglas cages in a room with controlled humidity and temperature and under a 12 hour light-dark cycle. Food and water were freely available ad lib.

Cell Culture

Bovine chromaffin cells were obtained from the laboratory of Dr. Jaqueline Sagen at the University of Chicago at Ill. Upon arrival, cells were plated using DMEM-F12 media with serum. Cell counts using the tryphan blue method revealed a total of $8 \times 10^{-6}$ per ml of surviving cells. A 95% viability of chromaffin cells were measured at the day of arrival and during the day of transplantation. Half of the chromaffin cells solution was co-cultured overnight with Sertoli cells.

The preparation of Sertoli cells is according to the method described by Selawry & Cameron (Selawry and Cameron, 1993), which is incorporated herein by reference. Specifically, the testes were removed, chopped into several pieces, and placed in a 50 ml conical tube containing 50 ml of Ham's F12/DMEM media. The pieces were washed once by centrifugation at 800×g for two minutes. The supernatant was aspirated, and the tissue resuspended in 40 ml of media containing 40 mg trypsin and 0.8 mg DNase in a sterile 250 ml Erlenmeyer flask. The flask was placed in an 37° C. oscillating incubator at 60–90 osc/minutes for 30 minutes. This step removed Leydig cells. The tubules were then transferred to a 50 ml conical tube, and centrifuged at 800×g for two minutes. The supernatant fraction was aspirated, and the pellet resuspended in 40 ml of 1M glycine, 2 mM EDTA containing 0.01% soybean trypsin inhibitor and 0.8 mg DNase, and incubated at room temperature for ten minutes. This step lysed any residual Leydig cells. The cells were washed by centrifugation for two minutes, and the step repeated twice, or until the media was no longer cloudy. The pellet was resuspended by gentle homogenization with a glass Pasteur pipet in 40 ml of media containing 20 mg collagenase in an Erlenmeyer flask, and incubated at 37° C. for five minutes with 60–90 osc/minutes. The cell suspension was centrifuged at 800×g for two minutes, and the pellet was resuspended by gentle homogenization with a Pasteur pipet in 40 ml media containing 40 mg collagenase and 0.2 mg DNase, and incubated in an Erlenmeyer flask at 37° C. for 30 minutes with 60–90 osc/minutes. The cells were then washed by centrifugation for two minutes, and the process repeated at least three times to eliminate peritubular cells. The cells were resuspended by gentle homogenization with a Pasteur pipet in 40 ml media containing 40 mg hyaluronidase and 0.2 mg of DNase, and incubated at 37° C. for 30 minutes with 60–90 osc/min. The cells were pelleted by soft centrifugation for two minutes, and washed at least five times to eliminate germ cells.

The resultant Sertoli cell-enriched fraction was resuspended into 0.25 ml of media with the chromaffin cells for at least 24 hours before transplantation. During the day of transplantation, the solution containing the Sertoli cell-enriched fraction and the chromaffin cells were resuspended using a Pasteur pipet then suctioned by a Hamilton syringe with a spinal needle of gauge 20.

Surgery

The surgical procedures were carried out in sterile conditions, as is well known in the art (Pakzaban et al., 1993). All animals were initially anesthetized with 0.60 ml/kg of sodium pentobarbital, then placed in Kopf stereotaxic instrument. Bilateral striatal transplants were performed with coordinates set at: anteroposterior=+1.2, medialateral=+/−2.8; dorsoventral—6.0, 5.9 & 5.8 (based on the atlas of Paxinos and Watson, 1984). The right hemisphere of the brain was transplanted with bovine chromaffin cells while the left hemisphere received chromaffin cells plus Sertoli cells. Each side received a total volume of 3 $\mu$l of the cell cocktail solution (1 $\mu$l per DV site). After surgery, the animals were placed in heating pads until recovery. Animals received a short course of immunosuppression using Cyclosporine-A (20 mg/kg/d,i.p.) immediately after surgery and on the day following the transplant. All animals were sacrificed at one month post transplant.

Histology

Animals were anesthetized with 0.70 ml/kg of sodium, then perfused with 500 ml of 0.9% isotonic saline and 500 ml paraformaldehyde. The animals were then decapitated, and the brain removed and post-fixed overnight in 40% paraformaldehyde with 30% sucrose in PBS. The following day, brain sections were cut at 30 microns using the Vibroslice (Campden Instrument, UK). Host tissue immunologic response was analyzed using the Lectin method (see below). Three experimenters conducted independent qualitative comparisons of the left and right side of the brain in a blind-randomized manner.

Lectin Method

Following vibrotome sectioning, brain sections were placed in 0.1% Triton X-100 for 15–30 minutes. The sections were then washed in 0.1M cationic PBS(pH 7.2), containing 0.1 mM $CaCl_2$, 0.1 mM $MgCl_2$. Incubation of sections was carried out in 20.0 µg/ml lectin made in cationic PBS at 4° C. for two hours. Rinsing, three times in PBS was done prior to incubation with DAB. The DAB stock solution was made by dissolving 10 mg DAB in 20 ml phosphate buffer (0.1M, pH 7.2) and adding 0.5 ml CoCl2 to DAB solution while stirring. Sections were first preincubated in DAB solution for 15 minutes. Upon adding 0.6 ml 3% $H_2O_2$ to 20.5 ml DAB solution, incubation lasted for five to ten minutes or until appropriate reaction was reached. Sections were again rinsed three times in PBS. Finally, sections were mounted from distilled water to wash out salts.

RESULTS

Figure 1B:
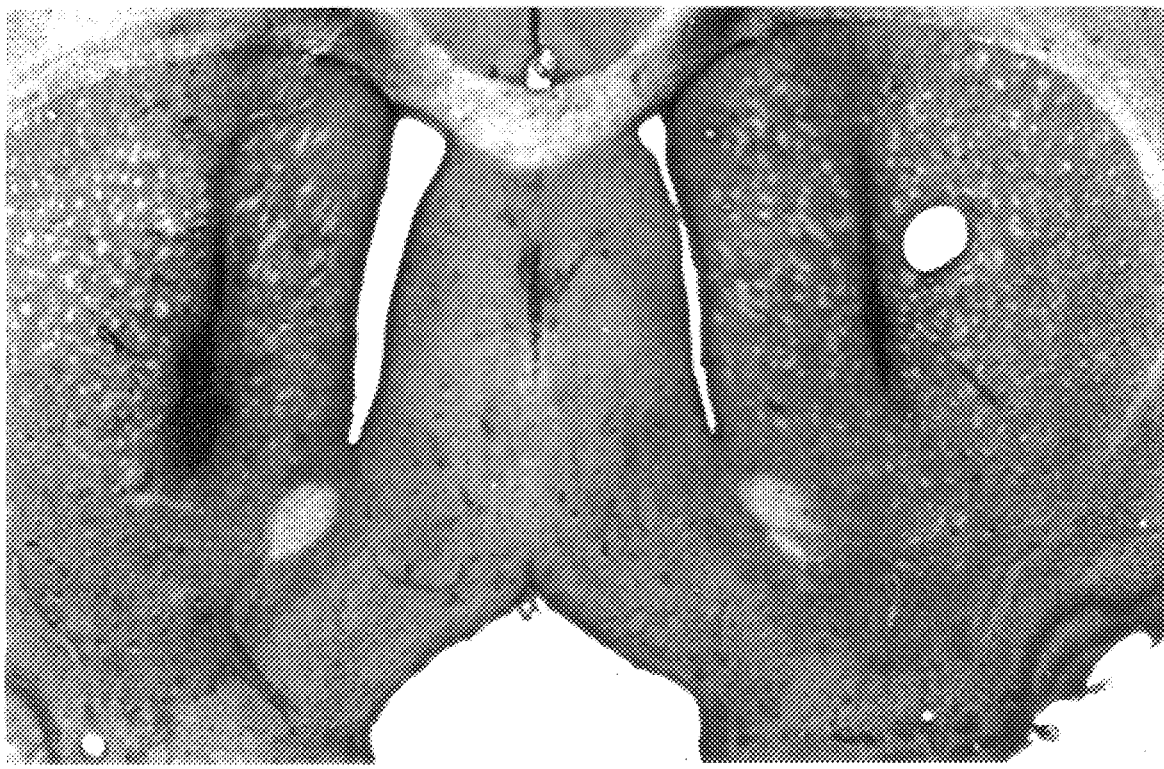
Figure 2A:
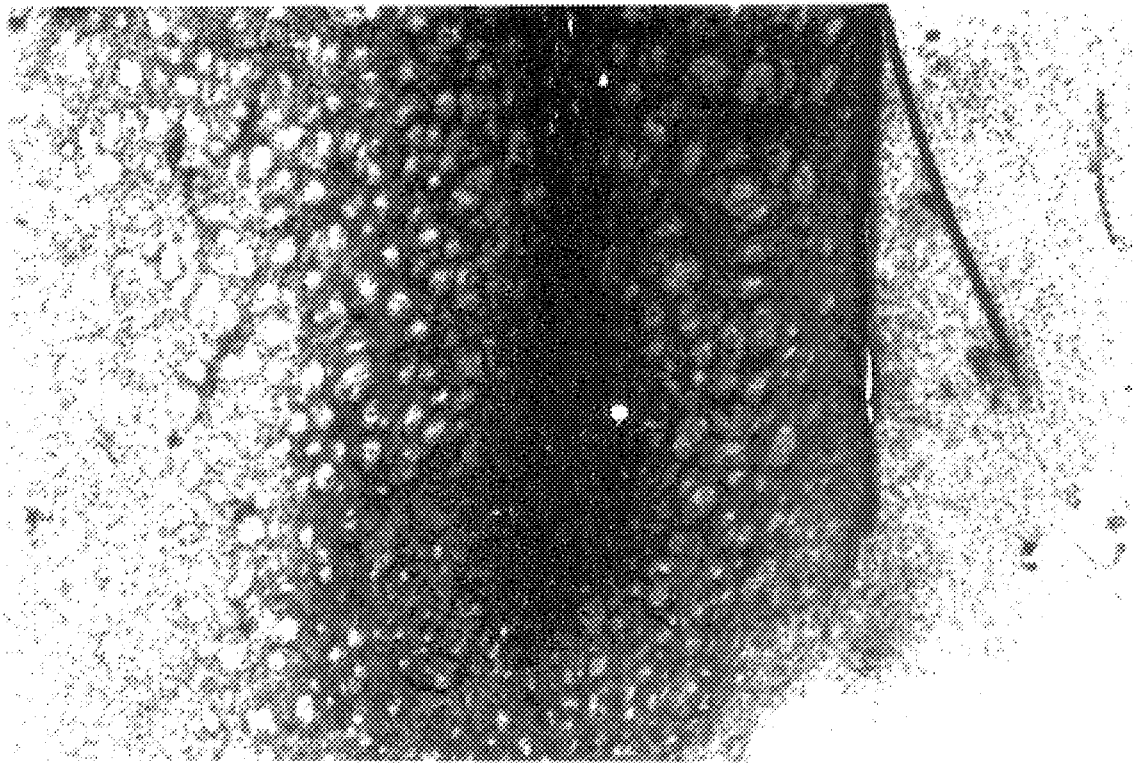
FIGS. 2a–d shows a higher magnification (20×1.25) from the photomicrograph of FIG. 1 of the transplant sites of brain sections illustrated in FIG. 1. The left panel (2a and c) showing chromaffin cells transplanted side while the right panel (2b and d) shows the side transplanted with chromaffin cells with Sertoli cells.
Figure 2B:
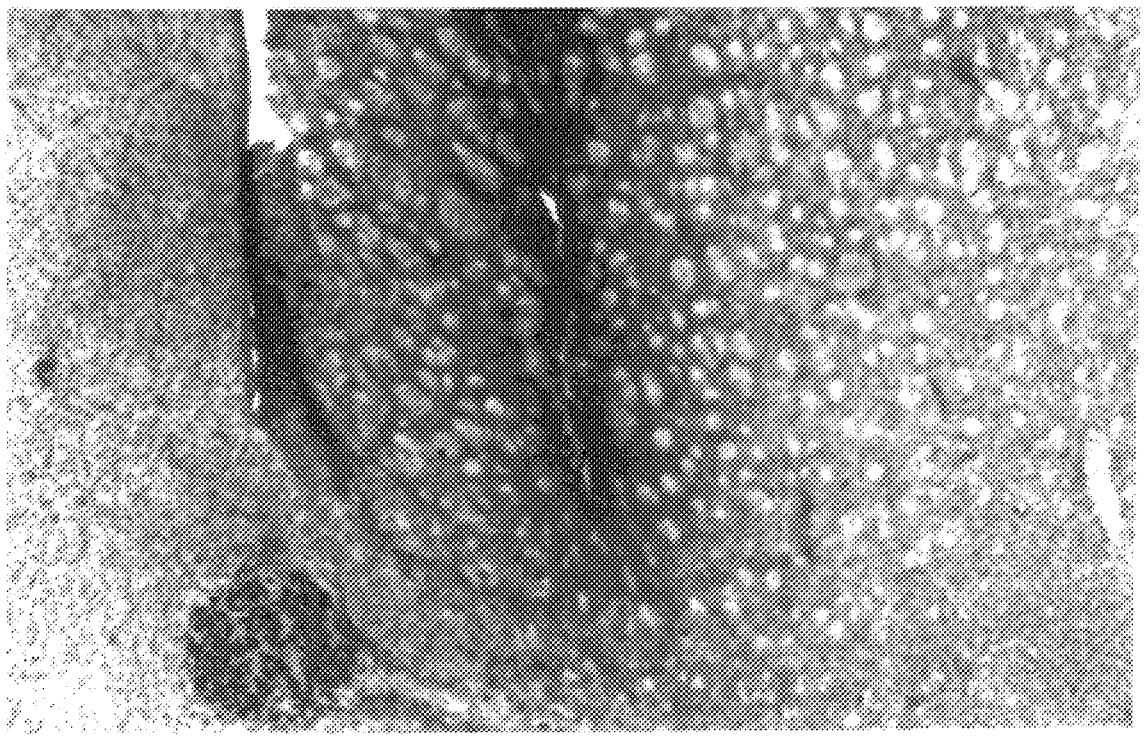
Figure 2C:
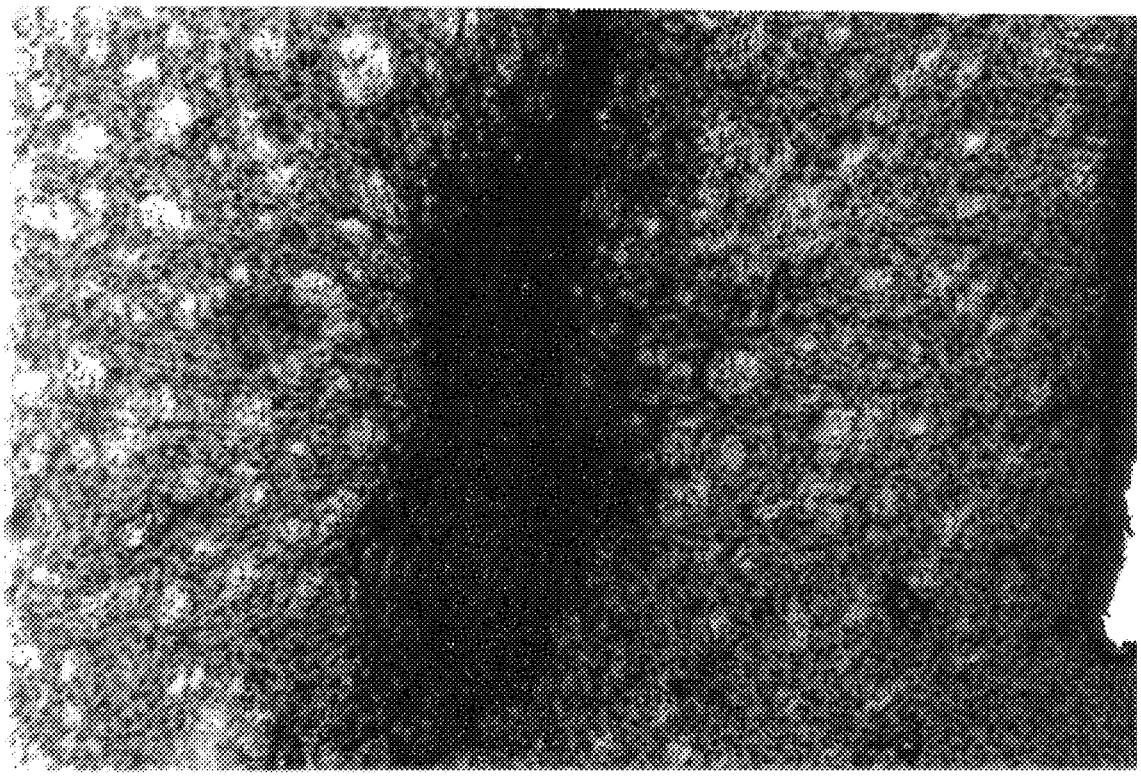
Figure 2D:
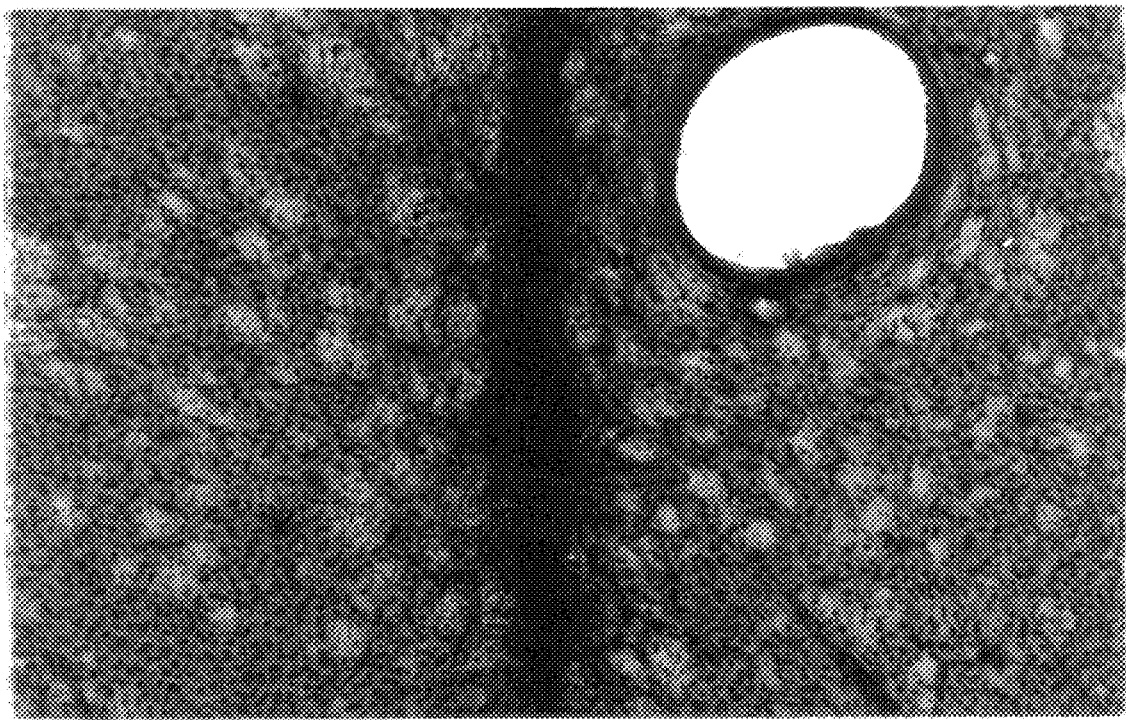

Histological analyses of both transplant sites revealed that the transplanted side with chromaffin cells alone with greater glial infiltration and higher number of macrophages than he transplanted side with chromaffin cells plus Sertoli cells (FIGS. 1 & 2). No significant difference in glial response was observed between animals treated with or without cyclosporine.

Two conclusions are made from the data:
1) a localized effect of the Sertoli cells which appeared to prevent immunologic response of the host tissue, and: 2) a sustained immunosuppression, with or without a short course of CsA administration, was achieved with simultaneous transplantation of chromaffin cells with Sertoli cells.

It can therefore be concluded that Sertoli cells can provide an immunologically privileged site in the CNS by direct intracranial infusion. Furthermore, with significant immunosuppression obtained following xenografts in the present study, Sertoli cells can provide greater beneficial effects on creating immunologically privileged sites following allografts.

Specific Protocol

The protocol involves three basic steps, Sertoli cell isolation, co-culture with neural specific cells and transplantation of the co-culture into the CNS (for details regarding the cell isolation see Selawry and Cameron (1993) and for details regarding cell transplantation see (Pakzaban et al., 1993).

1. Sertoli cell isolation

The isolation procedure follows a well-defined method as described in reference (Selawry and Cameron, 1993). The cell culture medium used in all isolation steps and in which the cell were incubated was DMEM:Hams F12 supplemented with retinol, ITS and gentamicin sulfate (Cameron and Muffly, 1991). Testes were surgically collected from sixteen day old male Sprague-Dawley rats. The testes were decapsulated and prepared for enzymatic digestion to separate other testicular cell types from the Sertoli cells. The enzymatic procedure using collagenase (0.1%), hyaluronidase (0.1%) and trypsin (0.25%) is routinely used in many cell isolation protocols. After sequential enzymatic digestion, the Sertoli cell isolate was washed with culture medium, transferred to sterile cell culture vessels and placed in a humidified, 5% $CO_2$-95% air tissue culture incubator. Following forty-eight hours of pre-incubation in a 39° C. incubator, the Sertoli cells were washed to remove any contaminating debris. The resultant Sertoli cell-enriched fraction was resuspended into 0.25 ml of DMEM/F12 medium, and incubated at 37° C. for at least 24 hours.

The Sertoli cells were liberated from the vessel floor with trypsin, transferred to a sterile conical test tube and repeatedly washed by centrifugation and then treated with trypsin inhibitor to cease the enzymatic action of trypsin. During the day of transplantation, the Sertoli cell-enriched fractions are resuspended and suctioned by a Hamilton syringe with a twenty gauge spinal needle.

2. Co-culture with neural specific cells

Sertoli cells and neural cell specific for transplantation for the neurodegenerative model were suspended by trypsin (0.01% 0), washed three times with medium and placed into a sterile cell culture vessel twenty-four hours prior to transplantation. The resulting co-culture was placed in a 5% $CO_2$-95% air incubator at 37° C. until utilized for transplantation.

3. Transplantation of co-culture into the CNS

The transplantation protocol follows the procedure as previously described in reference (Pakzaban et al., 1993). The animal surgery was carried out in sterile conditions. All animals were initially anesthetized with 0.60 ml/kg sodium pentobarbital, then placed in a Kopf stereotaxic instrument. For the Parkinson's disease model, unilateral striatal transplants are performed with coordinates set at: anteroposterior—+1.2, mediolateral—+/−2.9, dorsoventral—6.0, 5.9 and 5.8 (based on the atlas of Paxinos and Watson) (1984). Different coordinates will be used for different neurodegenerative animal models also based on Paxinos and Watson (1984). The striatum ipsilateral to the lesioned substantia nigra is transplanted with Sertoli cells or with the Sertoli cell co-culture. Each striatum receives a total volume of 3 µl of Sertoli cell or co-culture suspension. One microliter of the cell suspension was infused over one minute per dorsoventral site. Another five minutes was then allowed upon reaching the last dorsoventral site before retracting the needle. After surgery, the animals were placed on heating pads until they recovered. The animals received a short course of immunosuppression therapy using Cyclosporine-A (20 mg/kg/d, i.p.) immediately after surgery and on the day following the transplant.

Sertoli cells and/or co-culture suspensions are transplanted into animal models of various neurodegenerative disorders by stereotaxic coordinates defined for the specific disorder, as illustrated in the Parkinson's disease example. All experimental animals are systematically assayed for functional recovery by techniques specific to that animal model.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

What is claimed is:

1. A method of producing a sustained localized immunosuppressive effect in the brain by transplanting Sertoli cells proximate to the neural cells of the brain thereby forming an immunosuppressive Sertoli cell graft in the brain.

2. A method as set forth in claim 1 wherein the Sertoli cells are co-transplanted with neural cells including neuroendocrine cells into a mammal's brain, wherein said neural cells or said neuroendocrine cells form a graft.

3. A method as set forth in claim 2 wherein the neural cells or neuroendrocrine cells are first co-cultured with the Sertoli cells establishing co-cultured cells and the co-cultured cells are co-transplanted.

4. A method as set forth in claim 1 wherein said transplanting step is further defined as direct infusing of the Sertoli cells into the brain of a host.

* * * * *

UNITED STATES PATENT AND TRADEMARK OFFICE
CERTIFICATE OF CORRECTION

PATENT NO. : 5,830,460
DATED      : November 3, 1998
INVENTOR(S): Paul R. Sanberg et al.

It is certified that error appears in the above-indentified patent and that said Letters Patent is hereby corrected as shown below:

On the title page, item [75], delete "Richard Heller, Brandon," as an inventor.

Signed and Sealed this

Thirty-first Day of August, 1999

*Attest:*

Q. TODD DICKINSON

*Attesting Officer*     *Acting Commissioner of Patents and Trademarks*